(12) United States Patent
Tsuyuki (10) Patent No.: US 7,164,745 B2
(45) Date of Patent: Jan. 16, 2007

(54) X-RAY CT APPARATUS (75) Inventor: Masaharu Tsuyuki, Tochigi (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/882,359

(22) Filed: Jul. 2, 2004

(65) Prior Publication Data
US 2005/0047541 A1 Mar. 3, 2005

(30) Foreign Application Priority Data
Aug. 25, 2003 (JP) ............................ 2003-300307
Sep. 30, 2003 (JP) ............................ 2003-342383

(51) Int. Cl.
*A61B 6/00* (2006.01)

(52) U.S. Cl. ........................................................ 378/4

(58) Field of Classification Search ............... 378/4–20
See application file for complete search history.

(56) References Cited

U.S. PATENT DOCUMENTS 6,373,916 B1 * 4/2002 Inoue et al. .................... 378/4
6,580,777 B1 * 6/2003 Ueki et al. .................... 378/17

FOREIGN PATENT DOCUMENTS

JP 2001-61833 3/2001

* cited by examiner

*Primary Examiner*—Courtney Thomas
(74) *Attorney, Agent, or Firm*—Oblon, Spivak, McClelland, Maier & Neustadt, P.C.

(57) ABSTRACT

An X-ray CT apparatus comprises an X-ray radiation source configured to radiate X-rays toward an object, an X-ray detector including a plurality of X-ray detection segments, each of which includes a plurality of detection elements, a rotation control unit configured to control rotation of the X-ray radiation source, a reconstruction unit configured to reconstruct a tomographic image based on data collected by the X-ray detector. As one aspect of the X-rays CT apparatus, there is provided a fluoroscopic image creation unit configured to create a fluoroscopic image on a plane that crosses X-ray path connecting focus of the X-ray source to the center of the X-ray detector. As another aspect of the X-rays CT apparatus, there is provided an X-ray detector which is shaped arc. As another aspect of the X-rays CT apparatus, there is provided an operation unit configured to operate a position of the X-ray radiation source. As another aspect of the X-rays CT apparatus, there is provided a data conversion unit configured to convert cone beam data into parallel beam data and a fluoroscopic image creation unit configured to create a fluoroscopic image on a plane based on the parallel beam data.

14 Claims, 6 Drawing Sheets

X-RAY CT APPARATUS

CROSS-REFERENCE TO RELATED APPLICATIONS

This application is based upon and claims the benefit of priority from prior Japanese Patent Application Nos. P2003-300307 filed on Aug. 25, 2003, and P2003-342383 filed on Sep. 30, 2003, the entire contents of which are incorporated herein by reference.

FIELD OF THE INVENTION

The present invention relates to an X-ray CT apparatus.

BACKGROUND OF THE INVENTION

In a third generation X-ray CT apparatus, an X-ray tube is positioned opposite an X-ray detector that has several detection segments, each of which has a plurality of detection elements. A patient is located between the X-ray tube and the X-ray detector. The X-ray tube and the X-ray detector rotate around the patient, such as 360 degrees, and X-rays are radiated from the X-ray tube to the patient. X-rays penetrated though the patient are detected by the X-ray detector as projection data. A tomographic image is reconstructed by a reconstruction equipment based on the projection data. Thus, the X-ray CT apparatus generally obtains the tomographic image, however, not only tomographic image but also fluoroscopic image of interested part of the patient can be needed in a surgery. It may be possible to set both X-ray CT apparatus and X-ray TV apparatus in the same surgery room, but it is difficult to install these two large sized apparatuses because a space in the surgery room restricted.

Japanese Patent Disclosure (Kokai 7-231888, pp 3–4, FIG. 1) describes that a fluoroscopic image is obtained by a 2-dimensional X-ray detector located opposite an X-ray tube, and a tomographic image and a 3D image are obtained based on projection data obtained by the same X-ray detector. Thereby, since the fluoroscopic image and the tomographic image are obtained by a single apparatus, the surgery room can be effectively used. The CT apparatus described in Japanese Patent Disclosure (Kokai 7-231888, pp 3–4, FIG. 1) has two X-ray detectors that are arranged mutually in the position of 90 degrees in order to obtain fluoroscopic images from two directions, which makes it easy to lead a needle or a catheter in a percutaneous surgery.

Japanese Patent Disclosure (Kokai 11-146874, pp 4, FIG. 1) describes that an X-ray film cassette or an X-ray flat detector is arranged in the position corresponding to an X-ray detector of X-ray CT apparatus. However, with this CT apparatus, it is necessary to set the X-ray film cassette or the X-ray flat detector at a predetermined position when a fluoroscopy image is obtained. With this CT apparatus, a collimator is set such that X-rays shape a sector in obtaining the tomographic image, and X-rays shape a cone in obtaining the fluoroscopic image. However, with the X-ray CT apparatus described in Japanese Patent Disclosure (Kokai 7-231888, pp 3–4, FIG. 1), the fluoroscopic image is distorted because the X-ray detector is arc shaped. With the X-ray CT apparatus described in Japanese Patent Disclosure (Kokai 11-146874, pp 4, FIG. 1), when the fluoroscopic image is obtained, it is necessary to set the X-ray film cassette or the X-ray flat detector, which makes it difficult to perform real time imaging.

SUMMARY OF THE INVENTION

One object of the present invention is to ameliorate the above-mentioned problems. According to one aspect of the present invention, there is provided an X-ray CT apparatus comprising an X-ray radiation source configured to radiate X-rays toward an object, an arc shaped X-ray detector including a plurality of X-ray detection segments, each of which includes a plurality of detection elements, a rotation control unit configured to control rotation of the X-ray radiation source, a reconstruction unit configured to reconstruct a tomographic image based on data collected by the X-ray detector, and a fluoroscopic image creation unit configured to create a fluoroscopic image on a plane that crosses X-ray path connecting focus of the X-ray source to the center of the X-ray detector.

According to another aspect of the present invention, there is provided an X-ray CT apparatus comprising an X-ray radiation source configured to radiate X-rays toward an object, an X-ray detector including a plurality of X-ray detection segments, each of which includes a plurality of detection elements, a rotation control unit configured to control rotation of the X-ray radiation source, a cylindrical cover configure to cover the X-ray radiation source and the X-ray detector, a reconstruction unit configured to reconstruct a tomographic image based on data collected by the X-ray detector, and an operation unit configured to operate a position of the X-ray radiation source.

According to another aspect of the present invention, there is provided an X-ray CT apparatus comprising an X-ray radiation source configured to radiate cone beam X-rays toward an object, an arc shaped X-ray detector including a plurality of X-ray detection segments, each of which includes a plurality of detection elements, a rotation control unit configured to control rotation of the X-ray radiation source, a reconstruction unit configured to reconstruct a tomographic image based on cone beam data collected by the X-ray detector, a data conversion unit configured to convert the cone beam data into parallel beam data, and a fluoroscopic image creation unit configured to create a fluoroscopic image on a plane based on the parallel beam data.

According to another aspect of the present invention, there is provided an X-ray CT apparatus comprising an X-ray radiation source configured to radiate X-rays toward an object, an arc shaped X-ray detector including a plurality of X-ray detection segments, each of which includes a plurality of detection elements, a rotation control unit configured to control rotation of the X-ray radiation source, a reconstruction unit configured to reconstruct a tomographic image based on data collected by the X-ray detector when the X-ray radiation source rotates, and an operation unit configured to operate position of the X-ray radiation source, and a fluoroscopic image creation unit configured to create a fluoroscopic image on a plane that crosses X-ray path connecting focus of the X-ray source to the center of the X-ray detector based on data collected by the X-ray detector when the rotation of the X-ray radiation source stops.

According to another aspect of the present invention, there is provided an X-ray CT apparatus comprising means for radiating X-rays toward an object, an arc shaped X-ray detector including a plurality of X-ray detection segments, each of which includes a plurality of detection elements, means for controlling rotation of the means for radiating the X-rays, means for reconstructing a tomographic image based on data collected by the X-ray detector when the means for radiating the X-rays rotates, and means for operating position of the means for radiating the X-rays and means for creating a fluoroscopic image on a plane that crosses X-ray path connecting focus of the means for radiating the X-rays to the center of the X-ray detector based on data collected by the X-ray detector when the rotation of the means for radiating the X-rays stops.

According to another aspect of the present invention, there is provided a method for controlling an X-ray CT apparatus comprising radiating X-rays toward an object by an X-ray radiation source, detecting the X-rays by an arc shaped X-ray detector including a plurality of X-ray detection segments, each of which includes a plurality of detection elements, controlling rotation of the X-ray radiation source by a rotation control unit, reconstructing a tomographic image based on data collected by the X-ray detector when the X-ray radiation source rotates by a reconstruction unit, operating position of the X-ray radiation source by an operation unit; and creating a fluoroscopic image on a plane that crosses X-ray path connecting focus of the X-ray source to the center of the X-ray detector based on data collected by the X-ray detector when the rotation of the X-ray radiation source stops by a fluoroscopic image creation unit.

BRIEF DESCRIPTION OF THE DRAWINGS

A more complete appreciation of the invention and many of the attendant advantages thereof will be readily obtained as the same becomes better understood by reference to the detailed description when considered in connection with the accompanying drawings. In the drawings.

DETAILED DESCRIPTION OF EXEMPLARY EMBODIMENTS OF THE INVENTION

Figure 1:
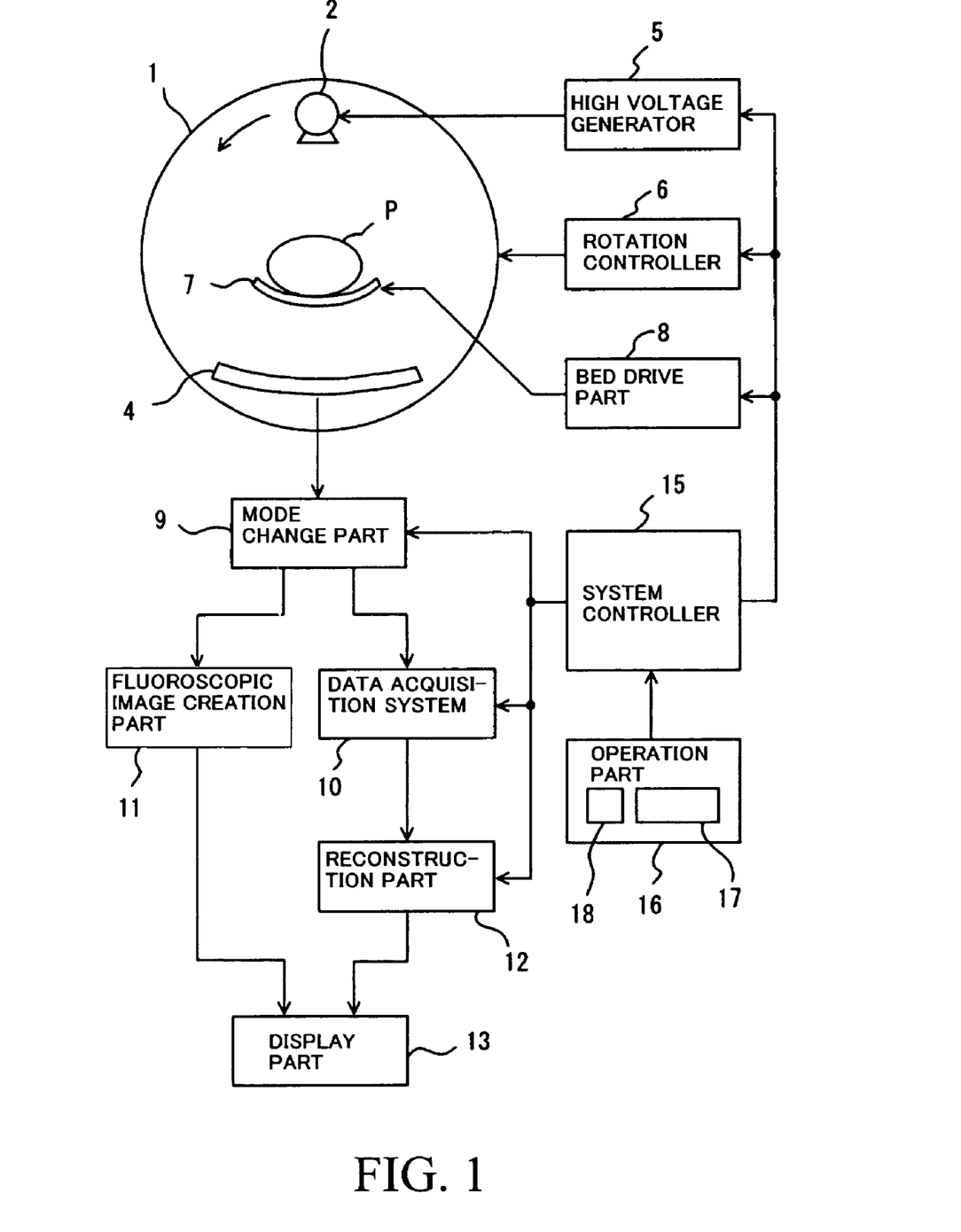
FIG. 1 is a block diagram of an X-ray CT apparatus according to a first embodiment.

Hereafter, a first embodiment of an X-ray CT apparatus is explained in detail with reference to FIG. 1 through FIG. 6. FIG. 1 is a block diagram of the first embodiment of the X-ray CT apparatus. The X-ray CT apparatus includes a gantry 1, an X-ray tube 2 that radiates X-rays toward a patient P, and an X-ray detector 4 that is positioned opposite the X-ray tube 2 such that the patient P is located therebetween. The X-ray detector 4 detects X-rays penetrated through the patient P. The X-ray tube 2 and the X-ray detector 4 rotate together with the gantry 1. Tube voltage and tube current are supplied to the X-ray tube 2 by the high voltage generator 5. These values are suitably changed according to CT mode or fluoroscopy mode that are mentioned below. The gantry 1 is controlled by a rotation controller 6 to be rotated in a predetermined direction in the CT mode. On the other hand, in the fluoroscopy mode, the gantry 1 rotates in a right direction or an opposite left direction by a predetermined angle according to operation of an operator. A bed plate 7 that the patient P is put on is positioned between the X-ray tube 2 and the X-ray detector 4. The bed drive part 8 controls the bed plate 7 to move in a body axis direction of the patient P (back or forward direction), or in right or left direction (width direction), or in vertical direction (up or down direction).

Figure 2:
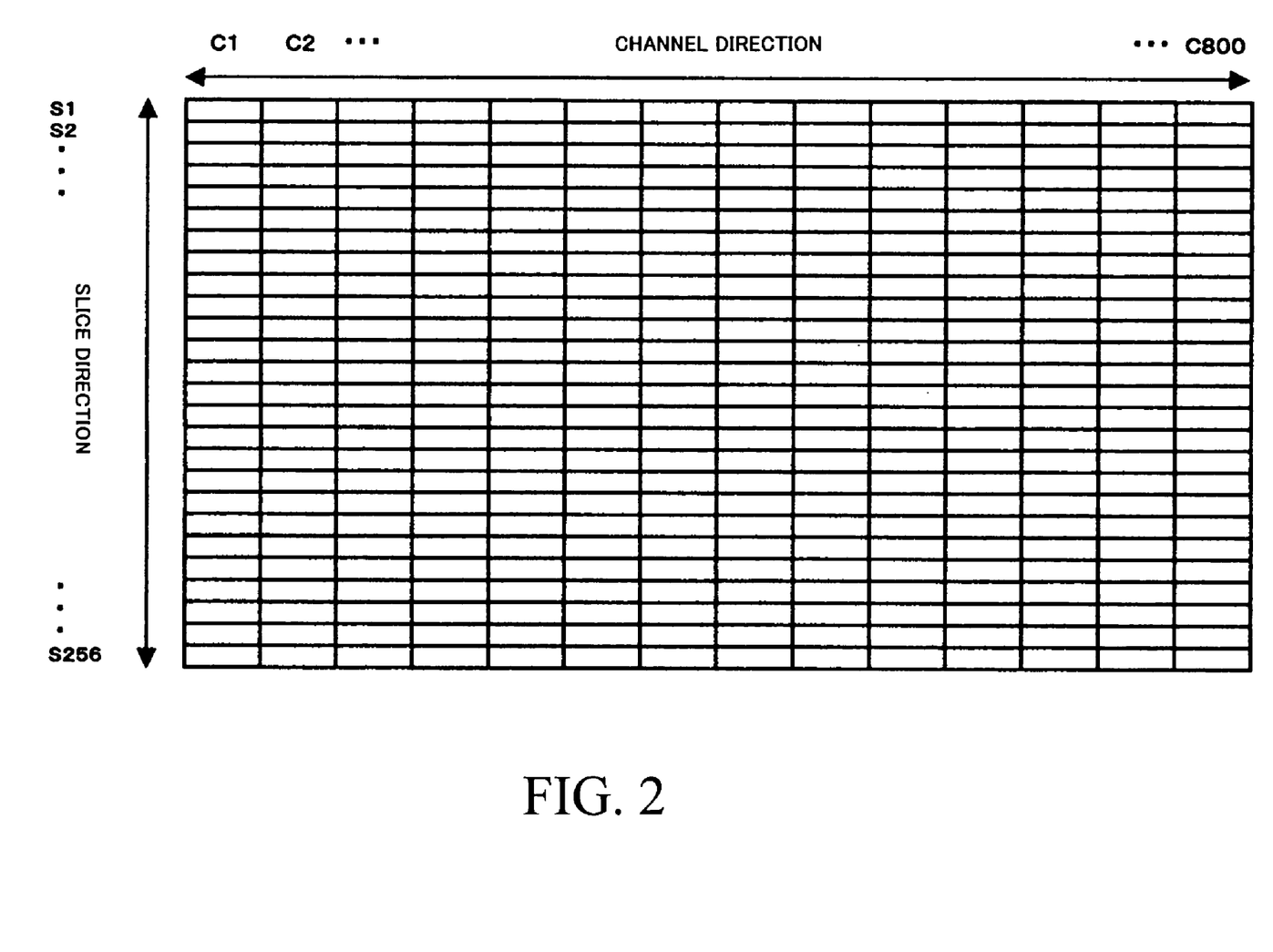
FIG. 2 is an upper view of an X-ray detector according to the first embodiment.

As shown in FIG. 2, the X-ray detector 4 forms a multi slice detector that includes a plurality of detection segments, such as 256 segments (S1–S256), arranged in a slice direction (body axis direction). Each detection segment includes a plurality of detection elements, such as 800 channels (C1–C800), arranged according to spread of X-rays radiated from the X-ray tube 2. A mode change part 9 is connected to output of the X-ray detector 4. By the mode change part 9, the output is alternatively supplied to a data acquisition system 10 or a fluoroscopic image creation part 11 according to selection of the CT mode or the fluoroscopy mode. Output of the data acquisition system 10 is supplied to a reconstruction part 12 which reconstructs a tomographic image based on data collected by the data acquisition system 10. A display part 13 displays the reconstructed tomographic image. The fluoroscopic image created by the fluoroscopic image creation part 11 is also supplied to the display part 13. The display part 13 includes a plurality of display monitors, such as TV monitors, and the tomographic image and the fluoroscopic image are displayed on separate display monitors. The X-ray CT apparatus includes a system controller 15, including a computer and memory, that centrally controls each part. The X-ray CT apparatus further includes an operation part 16 with which an operator inputs each value or instruction to the system controller 15. The operation part 16 includes a touch panel on which the instruction is displayed as graph and character and with which the displayed item is operated by finger of the operator. The operation part 16 further includes an X-ray position indicator 18 indicating a position of the X-ray tube 2 in the fluoroscopy mode.

An operation of the X-ray CT apparatus is explained below. The operator selects the CT mode where the tomographic image is obtained or the fluoroscopy mode where the fluoroscopic image is obtained like the X-ray TV apparatus with a mode changing switch of the operation part 16. When the CT mode is selected, the mode change part 9 is changed through the system controller 15 so that the output of the X-ray detector 4 is supplied to the data acquisition system 10. The system controller 15 controls the high voltage generator 5 to set the impression conditions of the high voltage to the X-ray tube 2 to appropriate value for obtaining the tomographic image, such as 120 kV tube voltage and 300 mA tube current. The system controller 15 further controls the gantry 1 to rotate at the rate of 0.5 second/rotation continuously in the predetermined direction. Since operation of the CT imaging is the same as or similar to that of usual X-ray CT apparatus, the explanation is omitted.

On the other hand, when the fluoroscopy mode is selected with the mode changing switch of the operation part 16, the mode change part 9 is changed through the system controller 15 so that the output of the X-ray detector 4 is supplied to the fluoroscopic image creation part 11. The tube voltage and the tube current impressed to X-ray tube 2 are changed to appropriate values for fluoroscopic imaging, such as 120 kV and 100 mA, by the high voltage generator 5. In the fluoroscopy mode, X-ray dose per unit time is smaller than X-ray dose in the CT mode. As an example, the tube current of X-ray tube 2 in the fluoroscopy mode is set up lower than the tube current of X-ray tube 2 in the CT mode. In the fluoroscopy mode, the rotation controller 6 stops continuous rotation of the gantry 1 under control of the system controller 15. For example, the X-ray tube 2 rotates by a predetermined angle to right or left direction according to operation of the operator on the basis of the position in right above of the patient P.

In the fluoroscopy mode, the system controller 15 controls the rotation controller 6 to stop the X-ray tube 2 of the gantry 1 in a basic position of the right above of patient P. The operator positions the bed plate 7 to up or down direction, and right or left direction via the bed drive part 8 so that the patient P is located at an appropriate position for imaging. Furthermore, the operator sets the position of the X-ray tube 2 and the X-ray detector 4 to the patient P (radiation angle of the X-rays to the patient P). The setting of the position is performed with the touch panel 17 of the operation part 16.

Figure 3A:
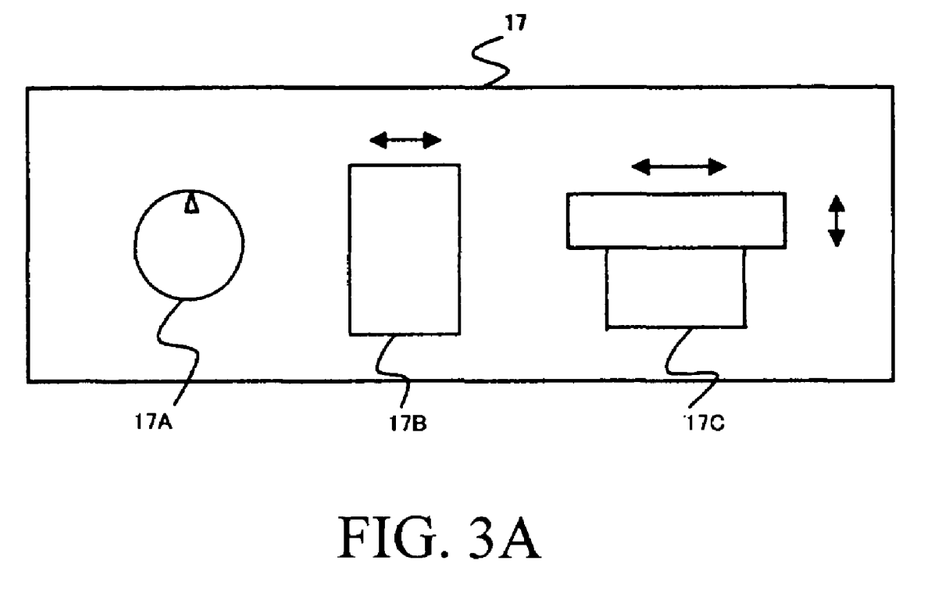
FIG. 3A is a view of a positioning operation device according to the first embodiment.
Figure 3B:
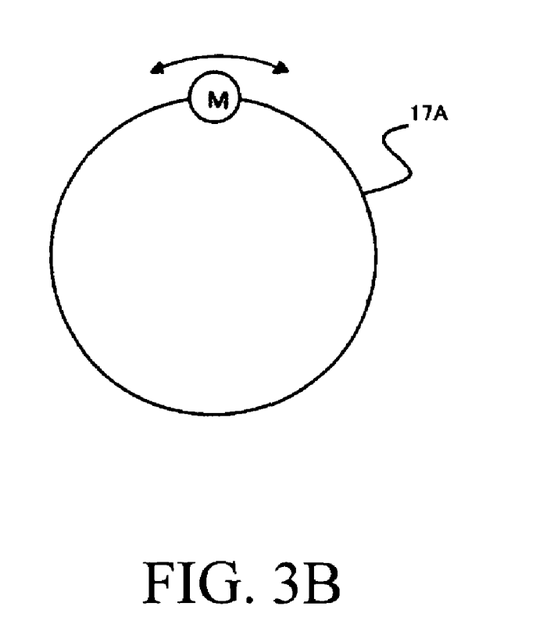
FIG. 3B is an enlarged view of the positioning operation device according to the first embodiment.

FIG. 3A shows a dial-shaped positioning operation part 17A for positioning the X-ray tube 2. FIG. 3B is enlarged view of the positioning operation part 17A. When the operator traces a mark M indicating the present position of the X-ray tube 2 to a desired position with finger, the information is transmitted to the system controller 15. The system controller 15 controls the rotation controller 6, and the gantry 1 rotates such that the X-ray tube 2 is located at the desired position. An angle position of the dial (Angle position of the mark M) corresponds to an angle of the position of the X-ray tube 2. As an arrow shows, the X-ray tube 2 can rotate both right and left directions. FIG. 3A further shows a bed operation part 17B for moving the bed plate 7 in the width direction. When the operator traces the arrow to a desired direction with finger, the information is transmitted to the system controller 15. The system controller 15 moves the bed drive part 8 in the width direction such that the patient P is located at the desired position. FIG. 3A further shows a bed operation part 17C for moving the bed plate 7 in the back and forward direction and up and down direction. When the operator traces the arrow to a desired direction with finger, the information is transmitted to the system controller 15. The system controller 15 moves the bed drive part 8 in the back and forward direction and the up and down direction such that the patient P is located at the desired position. The positioning operation part 17A may be included in the X-ray position indicator 18.

Figure 4:
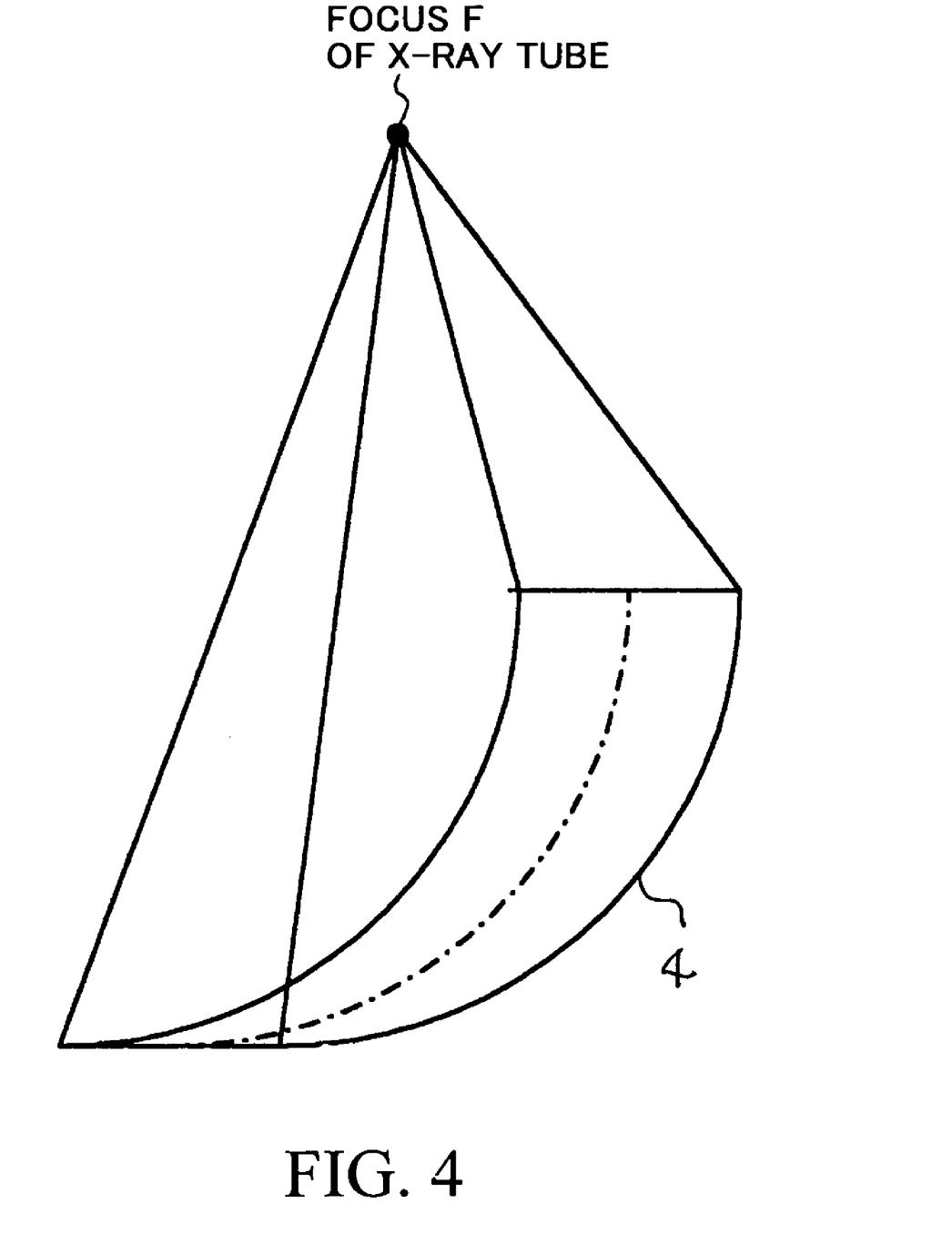
FIG. 4 is a view for explaining X-rays radiated from an X-ray tube to incidence surface of the X-ray detector.

When the position of the patient P and the radiation angle are determined, the operator starts the fluoroscopic imaging by pushing a button of the operation part. Appropriate voltage and current for fluoroscopic imaging, such as 120 kV and 100 mA, are impressed on the X-ray tube 2 by the high voltage generator 5, and the X-rays are radiated to the patient P. FIG. 4 shows a state of the X-rays that are radiated from the X-ray tube 2 to the incidence surface of the X-ray detector 4. A collimator limits a radiation scope of the X-rays to the size of incidence surface of the X-ray detector 4.

Figure 5:
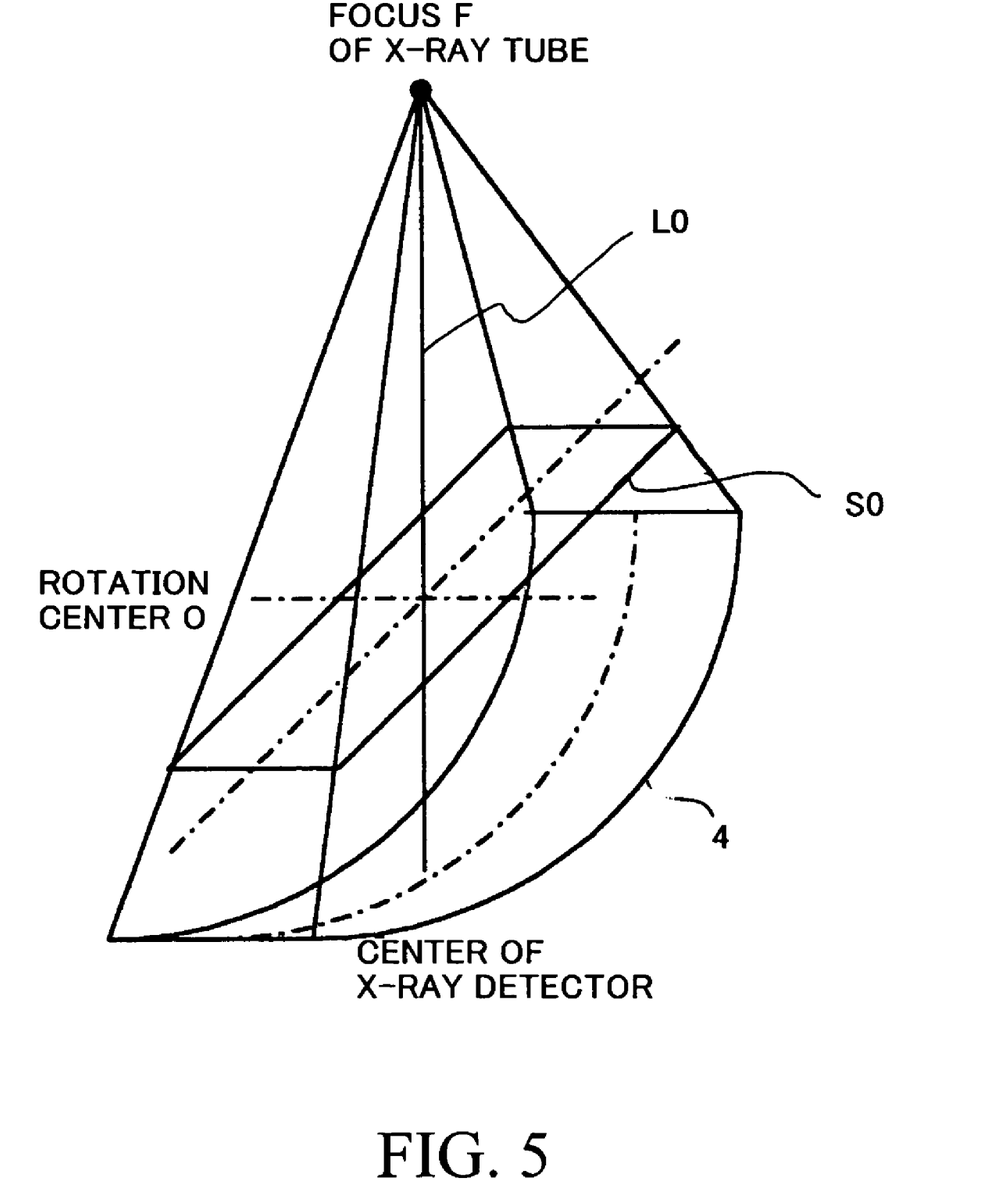
FIG. 5 is a view for explaining a plane where a fluoroscopic image is created.

Although the X-ray detector 4 is shown in FIG. 2 as an upper view, in fact, the incidence surface of the X-ray detector 4 curves as shown in FIG. 4 such that the distance from the focus F of X-ray tube 2 to each detection element is constant. That is, the shape of the X-ray detector 4 of the first embodiment is an arc. Therefore, when the fluoroscopy image of the patient P is displayed using the detection data of the X-ray detector 4 as it is, the fluoroscopy image is distorted. As shown in FIG. 5, the fluoroscopic image creation part 11 performs re-projection, based on the data from the X-ray detector 4, to a plane S0 that is perpendicular to X-ray path L0 connecting the focus F of the X-ray tube 2 to the center of the X-ray detector 4 or to a plane that is parallel to the plane S0. The re-projected image is displayed on the display part 13. The plane S0 is a plane that includes rotation center O of the gantry 1. The fluoroscopic image creation part sets a sampling time or frame addition such that frame rate is 30 frames per second, for example.

Figure 6:
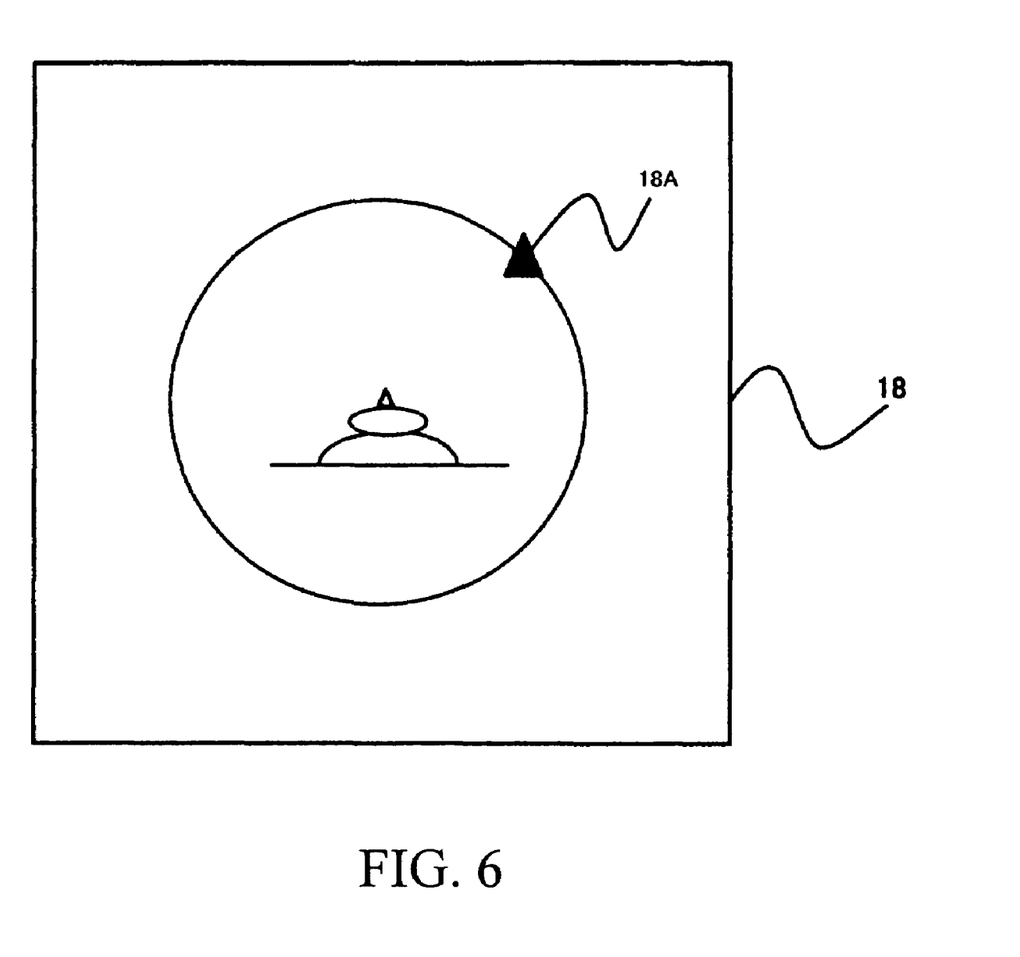
FIG. 6 is a displayed illustration indicating a position of an X-ray tube.

It is difficult to check from outside where the X-ray tube 2 is located since the gantry 1 is covered by a cover. It may be established for the operator to check where the X-ray tube 2 is located so that the operator sets the radiation angle to the patient P in the fluoroscopy mode. For instance, in the first embodiment, a encoder is attached to the gantry 1, and the X-ray position indicator 18 provided in the operation part 16 simply displays the position of the X-ray tube 2 based on signal from the encoder as shown in FIG. 6. For example, a mark 18A indicating the present position of the X-ray tube is displayed. The X-ray position indicator 18 may be combined with the positioning operation part 17A, and the mark 18A may indicate the X-ray tube position that is set by the operator. In the first embodiment, distortion of the fluoroscopic image that is obtained by the X-ray detector used for tomographic imaging can be reduced.

Not only the first embodiment but also other embodiments or modifications may be applied. For example, as a method for indicating the position of the X-ray tube, a plurality of LEDs may be arranged by 15 degrees around an aperture, where the patient P is located, of a cylindrical cover of the gantry 1. A LED corresponding to the position of the X-ray tube 2 illuminates based on the signal from the encoder attached to the gantry 1. Thereby, the position of the X-ray tube 2 can be indicated more visually. The LED may be arranged on a half round of the aperture that is above the bed plate 7 instead of all round.

A part of the gantry 1 around the aperture where the patient P is located may be transparent or translucent so that the X-ray tube 2 can be seen from outside. Thereby, the position of the X-ray can be checked without the indication, such as LEDs. However, illumination, such as LEDs may be attached to the X-ray tube 2. Thereby, the position of the X-ray tube can be checked more clearly trough the transparent or translucent part. Since the X-ray tube is usually covered with an exterior, "The X-ray tube is visible" or "The illumination is attached to the X-ray tube" may mean "The exterior of the X-ray tube is visible" or "The illumination is attached to the exterior of the X-ray tube".

As another modification, the X-ray CT apparatus may include a tilt mechanism configured to tilt a gantry 1. As another modification, the radiation scope of the X-rays in the fluoroscopy mode may be broader than the radiation scope of the X-rays in the CT mode. For example, in the CT mode, the X-rays may be radiated to the scope corresponding to 64 segments of 256 segments of the X-ray detector. On the other hand, in the fluoroscopy mode, the X-rays may be radiated to the scope corresponding to 256 segments of the X-ray detector.

As another modification, a flat panel detector may be continually rotated in the CT mode, and may be stopped at desired position in the fluoroscopy mode.

What is claimed is:

1. An X-ray CT apparatus, comprising
   an X-ray radiation source configured to radiate X-rays toward an object;
   an arc shaped X-ray detector including a plurality of X-ray detection segments, each of which includes a plurality of detection elements, said X-ray detector configured to detect X-rays via an X-ray path connecting a focus of the X-ray source to the X-ray detection segments;

a rotation control unit configured to control rotation of the X-ray radiation source;

a reconstruction unit configured to reconstruct a tomographic image based on data collected by the X-ray detector; and a fluoroscopic image creation unit configured to project data detected by the X-ray detector on a plane that crosses the X-ray path and to create a fluoroscopic image based on the projected data.

2. The X-ray CT apparatus according to claim 1, further comprising a cover configured to cover the X-ray radiation source and the X-ray detector.

3. The X-ray CT apparatus according to claim 2, wherein the rotation control unit stops the rotation of the X-ray radiation source; and the fluoroscopic image creation unit creates motion fluoroscopic image based on data repeatedly collected by the X-ray detector when the rotation of the X-ray radiation source stops.

4. The X-ray CT apparatus according to claim 2, further comprising an operation unit configured to operate a position of the X-ray radiation source.

5. The X-ray CT apparatus according to claim 4, wherein the rotation control unit stops the rotation of the X-ray radiation source at the position operated by the operation unit; and the fluoroscopic image creation unit creates motion fluoroscopic image based on data repeatedly collected by the X-ray detector when the rotation of the X-ray radiation source stops.

6. The X-ray CT apparatus according to claim 4 further comprising a position indication unit configured to indicate the position of the X-ray radiation source.

7. The X-ray CT apparatus according to claim 6, wherein the position indication unit is provided in the operation unit.

8. The X-ray CT apparatus according to claim 4, wherein the operation unit is a dial-shaped unit.

9. The X-ray CT apparatus according to claim 4, further comprising:

a bed plate on which the object is put;

a bed operation unit configured to set a position of the bed plate in at least one of a back or forward direction, a right or left direction and an up or down direction; and a bed drive part configured to control the bed plate based on the set position.

10. The X-ray CT apparatus according to claim 4, wherein the X-ray radiation source radiates high dose X-rays for obtaining data of tomographic image and radiates low dose X-rays for obtaining data of fluoroscopic image.

11. The X-ray CT apparatus according to claim 4, wherein the X-ray radiation source radiates the X-rays to a narrow scope in a body axis direction of the object for obtaining data of a tomographic image and radiates the X-rays to a broad scope in the body axis direction of the object for obtaining data of the fluoroscopic image.

12. The X-ray CT apparatus according to claim 4, wherein the rotation control unit controls the X-ray radiation source to rotate in a predetermined single direction for obtaining data of a tomographic image and controls the X-ray radiation source to rotate in at least one of two directions according to the position of the X-ray radiation source operated by the operation unit for obtaining data of the fluoroscopic image.

13. The X-ray CT apparatus according to claim 4, further comprising a tilt unit configured to tilt the X-ray radiation source and the X-ray detector.

14. A method for controlling an X-ray CT apparatus, comprising:

radiating X-rays toward an object by an X-ray radiation source;

detecting the X-rays by an arc shaped X-ray detector including a plurality of X-ray detection segments, each of which includes a plurality of detection elements, said X-ray detector configured to detect X-rays via an X-ray path connecting a focus of the X-ray source to the X-ray detection segments;

controlling rotation of the X-ray radiation source by a rotation control unit;

reconstructing a tomographic image based on data collected by the X-ray detector when the X-ray radiation source rotates by a reconstruction unit;

operating position of the X-ray radiation source by an operation unit; and projecting data detected by the X-ray detector on a plane that crosses the X-ray path and creating a fluoroscopic image based on the projected data.

* * * * *